(12) United States Patent
Baehner et al.

(10) Patent No.: US 9,187,564 B2
(45) Date of Patent: Nov. 17, 2015

(54) ANTIBODIES AGAINST HUMAN TWEAK AND USES THEREOF

(75) Inventors: Monika Baehner, Munich (DE); Hendrik Knoetgen, Penzberg (DE); Jens Niewoehner, Munich (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 922 days.

(21) Appl. No.: 13/250,485

(22) Filed: Sep. 30, 2011

(65) Prior Publication Data

US 2012/0121583 A1  May 17, 2012

(30) Foreign Application Priority Data

Oct. 5, 2010  (EP) .................................. 10186536

(51) Int. Cl.
    A61K 39/395  (2006.01)
    C07K 16/28  (2006.01)
    A61K 39/00  (2006.01)

(52) U.S. Cl.
    CPC ....... *C07K 16/2875* (2013.01); *A61K 2039/505* (2013.01); *C07K 2317/24* (2013.01); *C07K 2317/33* (2013.01); *C07K 2317/76* (2013.01); *C07K 2317/94* (2013.01)

(58) Field of Classification Search
    None
    See application file for complete search history.

(56) References Cited

U.S. PATENT DOCUMENTS

| | | | |
|---|---|---|---|
| 5,202,238 | A | 4/1993 | Fell, Jr. et al. |
| 5,204,244 | A | 4/1993 | Fell et al. |
| 2007/0110745 | A1 | 5/2007 | Rennert et al. |

FOREIGN PATENT DOCUMENTS

| CN | 1387538 | | 12/2002 |
|---|---|---|---|
| CN | 101171035 | | 4/2008 |
| CN | 101247830 | | 8/2008 |
| EP | 0307434 | B1 | 9/1993 |
| EP | 0698793 | B1 | 12/2004 |
| EP | 1878747 | A1 | 1/2008 |
| TW | 200740847 | | 11/2007 |
| TW | 201039847 | | 11/2010 |
| WO | 97/16064 | A1 | 5/1997 |
| WO | 98/05783 | A1 | 2/1998 |
| WO | 98/33523 | A1 | 8/1998 |
| WO | 98/52976 | A1 | 11/1998 |
| WO | 99/57134 | | 11/1999 |
| WO | 00/34317 | A2 | 6/2000 |
| WO | 00/34317 | A3 | 6/2000 |
| WO | 00/42073 | A1 | 7/2000 |
| WO | 03/086311 | A2 | 10/2003 |
| WO | 03/086311 | A3 | 10/2003 |
| WO | 2004/106381 | A1 | 12/2004 |
| WO | 2005/012493 | A2 | 2/2005 |
| WO | 2005/023872 | A1 | 3/2005 |
| WO | 2006/052926 | A2 | 5/2006 |
| WO | 2006/052926 | A3 | 5/2006 |
| WO | 2006/088890 | | 8/2006 |
| WO | 2006/089095 | A2 | 8/2006 |
| WO | 2006/089095 | A3 | 8/2006 |
| WO | 2006/089133 | A2 | 8/2006 |
| WO | 2006/096487 | | 9/2006 |
| WO | 2006/103100 | A2 | 10/2006 |
| WO | 2006/122187 | A2 | 11/2006 |
| WO | 2006/122187 | A3 | 11/2006 |
| WO | 2006/130374 | | 12/2006 |
| WO | 2006/130429 | A2 | 12/2006 |
| WO | 2006/130429 | A3 | 12/2006 |
| WO | 2006/133450 | A2 | 12/2006 |
| WO | 2007/002223 | A2 | 1/2007 |
| WO | 2007/024743 | A2 | 3/2007 |
| WO | 2007/024743 | A3 | 3/2007 |
| WO | 2007/071347 | A2 | 6/2007 |
| WO | 2007/071347 | A3 | 6/2007 |
| WO | 2008/057634 | A2 | 5/2008 |
| WO | 2008/057634 | A3 | 5/2008 |

OTHER PUBLICATIONS

Rudikoff et al. (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Michaelson et al. Results and Problems in Cell Differentiation New York, NY US:Springer-Verlag,:145-160 (Jan. 1, 2009).
Winkles et al., "Role of TWEAK and Fn14 in tumor biology" Frontiers in Bioscience 12:2761-2771 ( 2007).
Winkles et al., "TWEAK and Fn14: New Molecular targets for cancer therapy?" Cancer Letters 235(1):11-17 ( 2006).
Ausubel et al. Current Protocols in Molecular BiologyGreene and Wiley Interscience, New York, ( 1987).
Barnes et al., "Advances in Animal Cell Recombinant Production: GS-NS0 Expression System" Cytotechnology 32:109-123 ( 2000).

(Continued)

*Primary Examiner* — Laura B Goddard
*Assistant Examiner* — Meera Natarajan
(74) *Attorney, Agent, or Firm* — Diane L. Marschang

(57) ABSTRACT

The invention provides antibodies binding to TWEAK, including anti-TWEAK antibodies comprising a heavy chain variable domain CDR3 (CDR3H) selected from the group consisting of SEQ ID NO: 8, 16 or 24. The invention provides anti-TWEAK antibodies which are useful for the treatment of cancer, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

11 Claims, 1 Drawing Sheet

(56) References Cited

OTHER PUBLICATIONS

Barnes et al., "Characterization of the Stability of Recombinant Protein Production in the GS-NS0 Expression System" Biotech. Bioeng. 73:261-270 (2001).
Boackle et al., "An IgG primary sequence exposure theory for complement activation using synthetic peptides" Nature 282:742-3 (Dec. 1979).
Brueggemann et al., "Comparison of the effector functions of human immunoglobulins using a matched set of chimeric antibodies" J. Exp. Med. 166:1351-1361 (1987).
Brunhouse et al., "Isotypes of IgG: comparison of the primary structures of three pairs of isotypes which differ in their ability to activate complement" Mol Immunol 16(11):907-17 (Nov. 1979).
Burton, D.R. et al., "The C1q receptor site on immunoglobulin G" Nature 288:338-344 (1980).
Carter, P. et al., "Humanization of an anti-p185HER2 antibody for human cancer therapy" Proc. Natl. Acad. Sci. USA 89:4285-4289 (1992).
Chicheportiche et al., "TWEAK, a new secreted ligand in the tumor necrosis factor family that weakly induces apoptosis" J Biol Chem 272(51):32401-32410 (Dec. 19, 1997).
Deyl, Z. et al., Journal of Chromatography Library, "Advanced Chromatographic and Electromigration Methods in BioSciences" Amsterdam, The Netherlands: Elsevier Science BV, vol. 60:(entire book) (1998).
Durocher, Y. et al., "High-level and high-throughput recombinant protein production by transient transfection of suspension-growing human 293-EBNA1 cells" Nucleic Acids Research 30(2):e9 (2002).
Geisse et al., "Eukaryotic Expression Systems: A Comparison" Protein Expres Purif 8:271-282 (1996).
Heftmann, E., Chromatography "part A: fundamentals and techniques" fifth edition, Amsterdam, The Netherlands: Elsevier Science Publishing Company,:(entire book) (1992).
Hezareh et al., "Effector function of a panel of mutants of a broadly neutralizing antibody against human immunodeficiency virus type 1" J. of Virology 75(24):12161-12168 (2001).
Huston et al., "Protein engineering of single-chain Fv analogs and fusion proteins" Method Enzymol 203:46-88 (1991).
Idusogie et al., "Mapping of the C1q Binding Site on Rituxan, A Chimeric Antibody with a Human IgG1 Fc" J Immunol 164(8):4178-4184 (2000).
International Search Report for PCT/EP2011/058482, mailing dated Sep. 23, 2011.
Jefferis, B., "Glycosylation of recombinant antibody therapeutics" Biotechnol Prog 21:11-16 (2005).
Johne et al., "Epitope Mapping and Binding Kinetics of Monoclonal Antibodies Studies by Real Time Biospecific Interaction Analysis Using Surface Plasmon Resonance" Journal of Innunological Methods 160:191-198 (1993).
Johnson et al., "Kabat Database and its applications: 30 years after the first variability plot" Nucleic Acids Res 28(1):214-218 (2000).
Kabat et al. Sequences of Proteins if Immunological Interest, 5th edition, Diane Publishing (1992).
Kabat et al. Sequences of Proteins of Immunological Interest 5th edition, Bethesda, MD: Public Health Service, National Institute of Health, (1991).
Kaufman, "Overview of Vector Design for Mammalian Gene Expression" Mol Biotechnol 16:151-160 (2000).
Lonberg, "Human antibodies from transgenic animals" Nat Biotechnol 23(9):1117-1125 (Sep. 2005).
Love et al., "Recombinant antibodies possessing novel efector functions" Methods Enzymol. 158:515-527 (1989).
Lukas et al., "Inhibition of C1-Mediated Immune Hemolysis by Monomeric and Dimeric Peptides from the Second Constant Domain of Human Immunoglobulin G" J Immunol 127(6):2555-2560 (Dec. 1981).
Lynch et al., "TWEAK Induces Angiogenesis and Proliferation of Endothelial Cells" The Journal of Biological Chemistry 274(13):8455-8459 (Mar. 26, 1999).
Makrides, S., et al., "Components of Victors for Gene Transfer and Expression in mammalian cells" Protein Expression and Purification 17:183-202 (1999).
Marsters et al., "Identification of a Ligand for the Death-Domain-Containing Receptor Apo3" Curr Biol 8(9):525-528 (1998).
Mizuochi et al., "Structures of the sugar chains of mouse immunoglobulin G" Arch Biochem Biophys 257(2):387-394 (1987).
Morgan et al., "The N-terminal end of the CH2 domain of chimeric human IgG1 anti HLA-DR is necessary for C1q, FcγRI and FcγRIII binding" Immunology 86:319-324 (1995).
Morrison et al., "Chimeric human antibody molecules: Mouse antigen-binding domains with human constant region domains" P Natl Acad Sci USA 81:6851-6855 (Nov. 1984).
Neuberger et al., "A hapten-specific chimaeric IgE antibody with human physiological effector function" Nature 314:268-270 (Mar. 21, 1985).
Norderhug, L., et al., "Versatile vectors for transient and stable expression of recombinant antibody molecules in mammalian cells" J. of Immunol. Methods 204:77-87 (1997).
Orlandi et al., "Cloning Immunoglobulin Variable Domains for Expression by the Polymerase Chain Reaction" P Natl Acad Sci USA 86:3833-3837 (May 1989).
Parekh et al., "Association of rheumatoid arthritis and primary osteoarthritis with changes in the glycosylation pattern of total serum IgG" Nature 316:452-457 (1985).
Poole and Poole et al. Chromatography Today, New York: Elsevier Science Publishing Company,:(entire book) (1991).
Raju, "Glycosylation variations with expression systems and their impact on biological activity of therapeutic immunoglobulins" BioProcess International 1:44-53 (2003).
Riechmann et al., "Reshaping human antibodies for therapy" Nature 332:323-327 (Mar. 1988).
Routier et al., "The glycosylation pattern of a humanized IgGI antibody (D1.3) expressed in CHO cells" Glycoconjugate J 14:201-207 (1997).
Saba et al., "A study of immunoglobulin G glycosylation in monoclonal and polyclonal species by electrospray and matrix-assisted laser desorption/ionization mass spectrometry" Anal Biochem 305:16-31 (2002).
Sambrook et al, "Molecular Cloning: A Laboratory Manual" (Sections 4.21-4.41), Cold Spring Harbor Laboratory Press, 2nd edition, New York (1989).
Schlaeger et al., "Transient Gene Expression in Mammalian Cells Grown in Serum-free Suspension Culture" Cytotechnology 30:71-83 (1999).
Schlaeger, "The Protein Hydrolysate, Primatone RL, is a Cost-effective Multiple Growth Promoter of Mammalian Cell Culture in Serum-containing and Serum-free Media and Displays Anti-apoptosis Properties" J Immunol Methods 194:191-199 (1996).
Scopes, R. K. Protein Purification: Principles and Practice New York: Springer-Verlag New York, Inc., (1982).
Shaper et al., "β1,4-Galactosyltransferase and lactose biosynthesis: recruitment of a housekeeping gene from the nonmammalian vertebrate gene pool for a mammary gland specific function" J. Mamm. Gland Biol. Neopl. 3:315-324 (1998).
Taniguchi et al., "Structures of the sugar chains of rabbit immunoglobulin G: Occurrence of asparagine-linked sugar chains in Fab fragment" Biochem 24:5551-5557 (1985).
Thommesen et al., "Lysine 322 in the human IgG3 C(H)2 domain is crucial for antibody dependent complement activation" Mol Immunol 37(16):995-1004 (Nov. 2000).
Vijayalakshmi, "Antibody purification methods" Appl Biochem Biotech 75:93-102 (1998).
Werner, R., et al., "Appropriate mammalian expression systems for biopharmaceuticals" Drug Research 48:870-880 (1998).

* cited by examiner

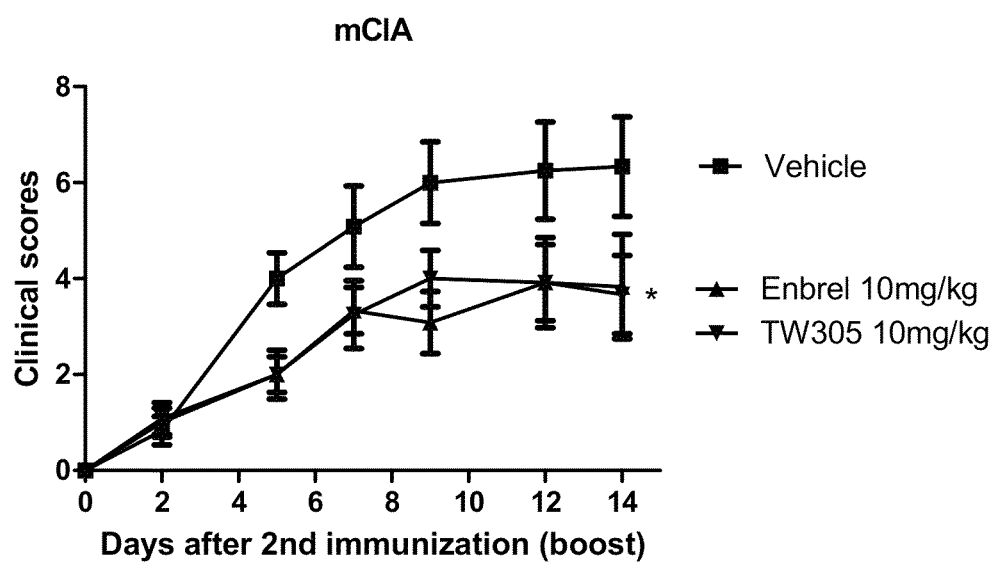

ANTIBODIES AGAINST HUMAN TWEAK AND USES THEREOF

RELATED APPLICATIONS

This application is a non-provisional application claiming priority to European Patent Application No. 10186536.8 filed Oct. 5, 2010, the contents of which are incorporated herein by reference.

FIELD OF THE INVENTION

The present invention relates to antibodies against human TWEAK (TWEAK antibodies), methods for their production, pharmaceutical compositions containing said antibodies, and uses thereof

BACKGROUND OF THE INVENTION

Human TWEAK (UniProtKB O43508, TNF-related weak inducer of apoptosis; SEQ ID NO: 60) is a cell surface associated type II transmembrane protein. TWEAK is described in Chicheportiche, Y., et al., J. Biol. Chem. 272 (1997) 32401-32410; Marsters, S. A., et al., Curr. Biol. 8 (1998) 525-528; Lynch, C. N., et al., J. Biol. Chem. 274 (1999) 8455-8459. The active form of TWEAK is a soluble homotrimer. Human and murine TWEAK show 93% sequence identity in receptor binding domain. The TWEAK receptor Fn14 (fibroblast growth factor inducible 14 kDa protein) is a 129 amino acid type I transmembane protein consisting of one single cystein rich domain in ligand binding domain. Signaling of TWEAK occurs via NF-KB pathway activation. TWEAK mRNA is expressed in a variety of tissues and found in most major organs like heart, brain, skeletal muscle, and pancreas, tissues related to the immune system like spleen, lymph nodes, and thymus. Fn14 mRNA has been detected in heart, brain, lung, placenta, vascular endothelial cells (EC) and smooth muscle cells. TWEAK-null and Fn14-null knockout mice are viable, healthy and fertile and have more natural killer cells and display an enhanced innate inflammatory response. TWEAK is involved in apoptosis, proliferation, angiogenesis, ischemic penumbra, cerebral edema, and multiple sclerosis.

Anti-TWEAK antibodies are mentioned in WO 1998/005783, WO 2000/042073, WO 2003/086311, WO 2006/130429, WO 2006/130374, WO 2006/122187, WO 2006/089095, WO 2006/088890, WO 2006/052926.

SUMMARY OF THE INVENTION

The invention comprises an antibody binding to human TWEAK, characterized in comprising as heavy chain variable domain CDR3 region (CDR3H) selected from the group consisting of SEQ ID NO: 8, 16 or 24.

The invention comprises a chimeric, humanized or T-cell epitope depleted variant of an antibody comprising a variable light chain of SEQ ID NO:1 and a variable heavy chain of SEQ ID NO:5, of an antibody comprising a variable light chain of SEQ ID NO:9 and a variable heavy chain of SEQ ID NO:13 or of an antibody comprising a variable light chain of SEQ ID NO:17 and a variable heavy chain of SEQ ID NO:21.

In one embodiment the antibody is characterized by comprising CDR1H of SEQ ID NO:6, CDR2H of SEQ ID NO:7, and CDR3H of SEQ ID NO:8.

In one embodiment the antibody is characterized by comprising CDR1H of SEQ ID NO:14, CDR2H of SEQ ID NO:15, and CDR3H of SEQ ID NO:16.

In one embodiment the antibody is characterized by comprising CDR1H of SEQ ID NO:22, CDR2H of SEQ ID NO:23, and CDR3H of SEQ ID NO:24.

In one embodiment the antibody is characterized by comprising CDR1H of SEQ ID NO:6, CDR2H of SEQ ID NO:7, CDR3H of SEQ ID NO:8 and CDR1L of SEQ ID NO:2, CDR2L of SEQ ID NO:3, CDR3L of SEQ ID NO:4.

In one embodiment the antibody is characterized by comprising CDR1H of SEQ ID NO:14, CDR2H of SEQ ID NO:15, CDR3H of SEQ ID NO:16 and CDR1L of SEQ ID NO:10, CDR2L of SEQ ID NO:11, CDR3L of SEQ ID NO:12.

In one embodiment the antibody is characterized by comprising CDR1H of SEQ ID NO:22, CDR2H of SEQ ID NO:23, CDR3H of SEQ ID NO:24 and CDR1L of SEQ ID NO:18, CDR2L of SEQ ID NO:19, CDR3L of SEQ ID NO:20.

In one embodiment the antibody is characterized by comprising as light chain variable domain sequence a sequence selected of the group consisting of SEQ ID NO:1, 9, 17, 25, 26, 27, 28, 29, 30, 31, 32, 33, 34, 35, 36, 56, or 58.

In one embodiment the antibody is characterized by comprising as heavy chain variable domain sequence a sequence selected from the group consisting of SEQ ID NO:5, 13, 21, 37, 38, 39, 40, 41, 42, 43, 44, 45, 46, 47, 48, 57, or 59.

In one embodiment the antibody is characterized by comprising as light chain variable domain sequence a sequence selected from the group consisting of SEQ ID NO:17, 25, 26, 27, 28, 29, 30, 31, 32, 33, 34, 35, or 36 and as heavy chain variable domain sequence a sequence selected from the group consisting of SEQ ID NO:21, 37, 38, 39, 40, 41, 42, 43, 44, 45, 46, 47, or 48.

In a preferred embodiment, the antibody is characterized by a combination of light and heavy variable chains selected from the group consisting of: 1/5, 9/13, 17/21, 25/37, 26/38, 27/39, 28/40, 29/41, 30/42, 31/43, 32/44; 33/45, 34/46, 35/47; 36/48, 56/57, 58/59.(e.g. 17/21 means an antibody comprising variable light chain of SEQ ID NO: 17 and variable heavy chain SEQ ID NO: 21).

One embodiment of the invention is an antibody binding to human TWEAK, characterized by comprising by comprising CDR1H of SEQ ID NO:6, CDR2H of SEQ ID NO:7, CDR3H of SEQ ID NO:8 and CDR1L of SEQ ID NO:2, CDR2L of SEQ ID NO:3, CDR3L of SEQ ID NO:4.

One embodiment of the invention is an antibody binding to human TWEAK, characterized by comprising CDR1H of SEQ ID NO:14, CDR2H of SEQ ID NO:15, CDR3H of SEQ ID NO:16 and CDR1L of SEQ ID NO:10, CDR2L of SEQ ID NO:11, CDR3L of SEQ ID NO:12.

One embodiment of the invention is an antibody binding to human TWEAK, characterized by comprising CDR1H of SEQ ID NO:22, CDR2H of SEQ ID NO:23, CDR3H of SEQ ID NO:24 and CDR1L of SEQ ID NO:18, CDR2L of SEQ ID NO:19, CDR3L of SEQ ID NO:20.

One embodiment of the invention is an antibody binding to human TWEAK, characterized by comprising a) a variable light chain of SEQ ID NO: 27 and a variable heavy chain of SEQ ID NO: 41, b) a variable light chain of SEQ ID NO: 27 and a variable heavy chain of SEQ ID NO: 44, c) a variable light chain of SEQ ID NO: 27 and a variable heavy chain of SEQ ID NO: 45, d), a variable light chain of SEQ ID NO: 26 and a variable heavy chain of SEQ ID NO: 47, e), a variable light chain of SEQ ID NO: 29 and a variable heavy chain of SEQ ID NO: 44, f), a variable light chain of SEQ ID NO: 31 and a variable heavy chain of SEQ ID NO: 45, or g) a variable light chain of SEQ ID NO: 29 and a variable heavy chain of SEQ ID NO: 41.

One embodiment of the invention is an antibody binding to human TWEAK, characterized by comprising a) a variable light chain of SEQ ID NO: 27 and a variable heavy chain of SEQ ID NO: 41, b) a variable light chain of SEQ ID NO: 27 and a variable heavy chain of SEQ ID NO: 44, c) a variable light chain of SEQ ID NO: 27 and a variable heavy chain of SEQ ID NO: 45, d) a variable light chain of SEQ ID NO: 26 and a variable heavy chain of SEQ ID NO: 47, e) a variable light chain of SEQ ID NO: 29 and a variable heavy chain of SEQ ID NO: 44, f) a variable light chain of SEQ ID NO: 31 and a variable heavy chain of SEQ ID NO: 45, g) a variable light chain of SEQ ID NO: 29 and a variable heavy chain of SEQ ID NO: 41, or h) a variable light chain of SEQ ID NO: 29 and a variable heavy chain of SEQ ID NO: 39.

These antibodies are designated as follows in the application.

| Antibody | SEQ ID NOs |
|---|---|
| 27 | 27, 41 |
| 28 | 27, 44 |
| 29 | 27, 45 |
| 30 | 26, 47 |
| 31 | 29, 44 |
| 32 | 31, 45 |
| 33 | 29, 41 |
| 34 | 29, 39 |

One embodiment of the invention is an antibody binding to human TWEAK, characterized by comprising a variable light chain of SEQ ID NO: 27 and a variable heavy chain of SEQ ID NO: 41, b) a variable light chain of SEQ ID NO: 27 and a variable heavy chain of SEQ ID NO: 45, c) a variable light chain of SEQ ID NO: 29 and a variable heavy chain of SEQ ID NO: 44, d) a variable light chain of SEQ ID NO: 29 and a variable heavy chain of SEQ ID NO: 41, or e) a variable light chain of SEQ ID NO: 29 and a variable heavy chain of SEQ ID NO: 39.

In one embodiment the antibody binding to TWEAK and being characterized by the above mentioned amino acid sequences and amino acid sequence fragments is of human IgG1 isotype, in one embodiment with mutations L234A and L235A. In one embodiment the antibody binding to TWEAK and being characterized by the above mentioned amino acid sequences and amino acid sequence fragments is of human IgG4 isotype, preferably with a mutations S228P and L235E.

An antibody according to the invention specifically binds to human TWEAK and preferably shows a half-life of a complex between soluble murine TWEAK (amino acids 81-225 of SEQ ID NO: 61) and antibody of 15 minutes or more at 25° C., measured by Biacore and binds to murine TWEAK and inhibits the interaction between murine TWEAK and Fn14 with an $IC_{50}$ value of 4.9 ng/ml or lower.

Preferably an antibody according to the invention shows a half-life of a complex between soluble human TWEAK (amino acids 99-249 of SEQ ID NO: 60) and antibody of 100 minutes or more, preferably of 110 minutes or more at 25° C., measured by Biacore. Anti-TWEAK antibodies showing such half-life are especially preferred for use in the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

Preferably an antibody according to the invention inhibits the interaction between human TWEAK and Fn14 with an $IC_{50}$ value of 3.5 ng/ml or lower, preferably 2.5 ng/ml or lower. As used herein, $IC_{50}$ means the amount of antibody that blocks 50% of the interaction between human TWEAK and Fn14.

The antibody is in one embodiment of human IgG1 isotype, in one embodiment with mutations L234A and L235A. In one embodiment the antibody according to the invention is of human IgG4 isotype, preferably with a mutations S228P and L235E. Preferably the antibody is a humanized or human antibody.

A further embodiment of the invention is a pharmaceutical composition comprising an antibody according to the invention.

A further embodiment of the invention is the use of an antibody according to the invention for the manufacture of a pharmaceutical composition.

A further embodiment of the invention is an antibody according to the invention for manufacture of a medicament for the treatment of cancer, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

A further embodiment of the invention is an antibody according to the invention for manufacture of a medicament for the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

A further embodiment of the invention an antibody according to the invention for manufacture of a medicament for the treatment of colon, lung, or pancreatic cancer.

A further embodiment of the invention is the use of an antibody according to the invention for manufacture of a medicament for the treatment of cancer, autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

A further embodiment of the invention is the use of an antibody according to the invention for manufacture of a medicament for the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

A further embodiment of the invention is the use of an antibody according to the invention for manufacture of a medicament for the treatment of colon, lung, or pancreatic cancer.

A further embodiment of the invention is a nucleic acid encoding an antibody according to the invention.

A further embodiment of the invention is a nucleic acid encoding a heavy chain variable domain and/or a light chain variable domain of an antibody according to the invention.

The invention further provides expression vectors containing nucleic acid according to the invention capable of expressing said nucleic acid in a prokaryotic or eukaryotic host cell, and host cells containing such vectors for the recombinant production of such an antibody.

The invention further comprises a prokaryotic or eukaryotic host cell comprising a vector according to the invention.

The invention further comprises a method for the production of a recombinant human or humanized antibody according to the invention, characterized by expressing a nucleic acid according to the invention in a prokaryotic or eukaryotic host cell and recovering said antibody from said cell or the cell culture supernatant. The invention further comprises the antibody obtainable by such a recombinant method.

Antibodies according to the invention show benefits for patients in need of a TWEAK targeting therapy. The antibodies according to the invention have new and inventive properties causing a benefit for a patient suffering from a cancer disease, especially suffering from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention further provides a method for treating a patient suffering from cancer, especially from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury, comprising administering to a patient diagnosed as having such a disease (and therefore being in need of such a therapy) an effective amount of an antibody binding to TWEAK according to the invention. The antibody is administered preferably in a pharmaceutical composition.

A further embodiment of the invention is a method for the treatment of a patient suffering from cancer, especially from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury, characterized by administering to the patient an antibody according to the invention.

The invention further comprises the use of an antibody according to the invention for the treatment of a patient suffering from cancer, especially from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury, and for the manufacture of a pharmaceutical composition according to the invention. In addition, the invention comprises a method for the manufacture of a pharmaceutical composition according to the invention.

The invention further comprises a pharmaceutical composition comprising an antibody according to the invention, optionally together with a buffer and/or an adjuvant useful for the formulation of antibodies for pharmaceutical purposes.

The invention further provides a pharmaceutical composition comprising an antibody according to the invention in a pharmaceutically acceptable carrier. In one embodiment, the pharmaceutical composition may be included in an article of manufacture or kit.

BRIEF DESCRIPTION OF THE FIGURES

FIG. 1 illustrates inhibition of collagen-induced arthritis, using a murine model of rheumatoid arthritis, by antibodies according to the invention

DETAILED DESCRIPTION OF THE INVENTION

The term "antibody" encompasses the various forms of antibody structures including, but not being limited to, whole antibodies, bispecific antibodies and antibody fragments. The antibody according to the invention is preferably a humanized antibody, chimeric antibody, or further genetically engineered antibody as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to TWEAK, namely being able to assemble together with a $V_H$ domain to a functional antigen binding site.

The terms "monoclonal antibody" or "monoclonal antibody composition" as used herein refer to a preparation of antibody molecules of a single amino acid composition.

The term "humanized antibody" refers to antibodies in which the framework and/or "complementary determining regions" (CDR) have been modified to comprise the CDR of an immunoglobulin of different species as compared to that of the parent immunoglobulin. In a preferred embodiment, a rabbit CDR is grafted into the framework region of a human antibody to prepare the "humanized antibody". See, e.g., Riechmann, L., et al., Nature 332 (1988) 323-327; and Neuberger, M. S., et al., Nature 314 (1985) 268-270.

The term "chimeric antibody" refers to a monoclonal antibody comprising a variable region, i.e., binding region, from mouse and at least a portion of a constant region derived from a different source or species, usually prepared by recombinant DNA techniques. Chimeric antibodies comprising for example a mouse variable region and a human constant region. Such mouse/human chimeric antibodies are the product of expressed immunoglobulin genes comprising DNA segments encoding rat immunoglobulin variable regions and DNA segments encoding human immunoglobulin constant regions. Other forms of "chimeric antibodies" encompassed by the present invention are those in which the class or subclass has been modified or changed from that of the original antibody. Such "chimeric" antibodies are also referred to as "class-switched antibodies." Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202,238 and 5,204,244.

The term "T cell epitope depleted antibody" refers to antibodies that were modified to remove or reduce immunogenicity by removing human T cell epitopes (peptide sequences within proteins with the capacity to bind to MHC Class II molecules). By this method, interactions between amino acid side chains of the peptide and specific binding pockets with the MHC class II binding groove are identified. The identified immunogenic regions are mutated to eliminate immunogenicity. Such methods are described in general in, e.g., WO 98/52976.

The terms "anti-TWEAK antibody" and "an antibody that specifically binds to TWEAK" according to the invention refer to an antibody that is capable of binding TWEAK with sufficient affinity such that the antibody is useful as a therapeutic agent in targeting TWEAK according to the invention. An antibody that binds specifically to TWEAK has a dissociation constant (Kd) of $10^{-9}$ M or less, e.g. from $10^{-9}$ M to $10^{-13}$ M.

The "variable domain" (variable domain of a light chain ($V_L$), variable domain of a heavy chain ($V_H$)) as used herein denotes each of the pair of light and heavy chain domains which are involved directly in binding the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention.

The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat et al., Sequences of Proteins of Immunological Interest, 5th ed., Public Health Service, National Institutes of Health, Bethesda, Md. (1991) and/or those residues from a "hypervariable loop".

The term "CDR1H" denotes the CDR1 region of the heavy chain variable region calculated according to Kabat. CDR2L, CDR3H, etc. mean the respective regions from the heavy(H) or light(L) chain. For example, an antibody characterized by comprising CDR1H of SEQ ID NO:6 means that the antibody comprises this amino acid sequence as a heavy chain variable chain CDR1 region in its variable heavy chain. For example, an antibody characterized by comprising CDR1H of SEQ ID NO:6, CDR2H of SEQ ID NO:7, CDR3H of SEQ ID NO:8 means that the antibody comprises in its heavy chain as sequence of CDR1 SEQ ID NO:6, as sequence of CDR2 SEQ ID NO:7, and as sequence of CDR3 SEQ ID NO:8.

The terms "nucleic acid" or "nucleic acid molecule" as used herein are intended to include DNA molecules and RNA molecules. A nucleic acid molecule may be single-stranded or double-stranded, but preferably is double-stranded DNA.

The term "amino acid" as used within this application denotes the group of naturally occurring carboxy a-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice.

As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibits various effector functions. An "Fc part of an antibody" is a term well known to the skilled artisan and defined on the basis of papain cleavage of antibodies. Depending on the amino acid sequence of the constant region of their heavy chains, antibodies or immunoglobulins are divided into the classes: IgA, IgD, IgE, IgG and IgM, and several of these may be further divided into subclasses (isotypes; the expressions "isotype" or "subclass" are used interchangeable herein), e.g. IgG1, IgG2, IgG3, and IgG4, IgA1, and IgA2. According to the heavy chain constant regions the different classes of immunoglobulins are called α, δ, ε, γ, and μ, respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described, e.g., by Boackle, R. J. et al., Nature 282 (1979) 742-743; Lukas, T. J. et al., J. Immunol. 127 (1981) 2555-2560; Brunhouse, R. and Cebra, J. J., Mol. Immunol. 16 (1979) 907-917; Burton, D. R. et al., Nature 288 (1980) 338-344; Thommesen, J. E. et al., Mol. Immunol. 37 (2000) 995-1004; Idusogie, E. E. et al., J. Immunol. 164 (2000) 4178-4184; Hezareh, M. et al., J. Virology 75 (2001) 12161-12168; Morgan, A. et al., Immunology 86 (1995) 319-324; EP 0 307 434. Such binding sites are, e.g., L234, L235, D270, N297, E318, K320, K322, P331, and P329 (numbering according to EU index of Kabat, see below). Antibodies of subclass IgG1, IgG2 and IgG3 usually show complement activation and C1q and C3 binding, whereas IgG4 does not activate the complement system and does not bind C1q and C3.

In one embodiment the antibody according to the invention comprises a Fc part derived from human origin and preferably all other parts of the human constant regions. As used herein the term "Fc part derived from human origin" denotes a Fc part which is either a Fc part of a human antibody of the subclass IgG1, IgG2, IgG3 or IgG4, preferably a Fc part from human IgG1 subclass, a mutated Fc part from human IgG1 subclass (preferably with a mutation on L234A and L235A), a Fc part from human IgG4 subclass or a mutated Fc part from human IgG4 subclass (preferably with a mutation on S228P and L235E). Mostly preferred are the human heavy chain constant regions of SEQ ID NO: 51 or SEQ ID NO: 52 (human IgG1 subclass), SEQ ID NO: 53 (human IgG1 subclass with mutations L234A and L235A), SEQ ID NO: 54 (human IgG4 subclass), or SEQ ID NO: 55 (human IgG4 subclass with mutations S228P and L235E).

Preferably the antibody according to the invention is of human IgG1 subclass or of human IgG4 subclass. In one embodiment the antibody according to the invention is of human IgG1 subclass. In one embodiment the antibody according to the invention is of human IgG4 subclass.

The antibody according to the invention is characterized in that the constant chains are of human origin. Such constant chains are well known in the state of the art and e.g. described by Kabat (see e.g. Johnson, G. and Wu, T. T., Nucleic Acids Res. 28 (2000) 214-218). For example, a useful human heavy chain constant region comprises an amino acid sequence of SEQ ID NO:51 or 28. For example, a useful human light chain constant region comprises an amino acid sequence of a kappa-light chain constant region of SEQ ID NO:49. It is further preferred that the antibody is of rabbit origin and comprises the antibody variable sequence frame of a rabbit antibody according to Kabat (see e.g. Sequences of Proteins of Immunological Interest, Kabat, E. A. et al., 5$^{th}$ edition, DIANE Publishing (1992)).

The invention comprises a method for the treatment of a patient in need of therapy, characterized by administering to the patient a therapeutically effective amount of an antibody according to the invention.

The invention comprises the use of an antibody according to the invention for therapy.

The invention comprises the use of an antibody according to the invention for the preparation of a medicament for the treatment of cancer, especially colon, lung, or pancreatic cancer or for the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention comprises the use of an antibody according to the invention for the treatment of cancer or inflammatory diseases, preferably for the treatment of colon, lung, or pancreatic cancer or for the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

A further embodiment of the invention is a method for the production of an antibody against TWEAK, characterized in that the sequence of a nucleic acid encoding the heavy chain of an antibody according to the invention and the nucleic acid encoding the light chain of said antibody are inserted into one or two expression vector(s), said vector(s) is/are inserted in a eukaryotic host cell, the encoded antibody is expressed and recovered from the host cell or the supernatant.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis).

Recombinant production of antibodies is well-known in the state of the art and described, for example, in the review articles of Makrides, S. C., Protein Expr. Purif. 17 (1999) 183-202; Geisse, S. et al., Protein Expr. Purif. 8 (1996) 271-282; Kaufman, R. J., Mol. Biotechnol. 16 (2000) 151-160; Werner, R. G., Arzneimittelforschung (Drug Res.) 48 (1998) 870-880.

The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including column chromatography and others well known in the art. See Ausubel, F. et al. (eds.), Current Protocols in Molecular Biology, Greene Publishing and Wiley Interscience, New York (1987).

Expression in NS0 cells is described by, e.g., Barnes, L. M. et al., Cytotechnology 32 (2000) 109-123; Barnes, L. M. et al., Biotech. Bioeng. 73 (2001) 261-270. Transient expression is described by, e.g., Durocher, Y. et al., Nucl. Acids. Res. 30 (2002) E9. Cloning of variable domains is described by Orlandi, R. et al., Proc. Natl. Acad. Sci. USA 86 (1989) 3833-3837; Carter, P. et al., Proc. Natl. Acad. Sci. USA 89 (1992) 4285-4289; Norderhaug, L. et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199.

Monoclonal antibodies are suitably separated from the culture medium by conventional immunoglobulin purification procedures such as, for example, protein A-Sepharose, hydroxylapatite chromatography, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Nucleic acid molecules encoding amino acid sequence variants of anti-TWEAK antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of humanized anti-TWEAK antibody.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g. a pharmaceutical composition, containing one or a combination of monoclonal antibodies, or the antigen-binding portion thereof, of the present invention, formulated together with a pharmaceutically acceptable carrier.

As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion.

A composition of the present invention can be administered by a variety of methods known in the art. As will be appreciated by the skilled artisan, the route and/or mode of administration will vary depending upon the desired results.

Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from cancer, especially from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention comprises also a method for the treatment of a patient suffering from such disease.

The invention further provides a method for the manufacture of a pharmaceutical composition comprising an effective amount of an antibody according to the invention together with a pharmaceutically acceptable carrier and the use of the antibody according to the invention for such a method.

The invention further provides the use of an antibody according to the invention in an effective amount for the manufacture of a pharmaceutical agent, preferably together with a pharmaceutically acceptable carrier, for the treatment of a patient suffering from cancer, especially from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

The invention also provides the use of an antibody according to the invention in an effective amount for the manufacture of a pharmaceutical agent, preferably together with a pharmaceutically acceptable carrier, for the treatment of a patient suffering from cancer, especially from colon, lung, or pancreatic cancer or from autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

DESCRIPTION OF THE SEQUENCES

TABLE 1

| Antibody 301 | |
|---|---|
| Rabbit variable domain of light chain (VL) | SEQ ID NO: 1 |
| CDR1L | SEQ ID NO: 2 |
| CDR2L | SEQ ID NO: 3 |
| CDR3L | SEQ ID NO: 4 |
| Rabbit variable domain of heavy chain (VH) | SEQ ID NO: 5 |
| CDR1H | SEQ ID NO: 6 |
| CDR2H | SEQ ID NO: 7 |
| CDR3H | SEQ ID NO: 8 |
| Chimeric light chain 301 | SEQ ID NO: 56 |
| Chimeric heavy chain 301 | SEQ ID NO: 57 |

TABLE 2

| Antibody 304 | |
|---|---|
| Rabbit variable domain of light chain (VL) | SEQ ID NO: 9 |
| CDR1L | SEQ ID NO: 10 |
| CDR2L | SEQ ID NO: 11 |
| CDR3L | SEQ ID NO: 12 |
| Rabbit variable domain of heavy chain (VH) | SEQ ID NO: 13 |
| CDR1H | SEQ ID NO: 14 |
| CDR2H | SEQ ID NO: 15 |
| CDR3H | SEQ ID NO: 16 |
| Chimeric light chain 304 | SEQ ID NO: 58 |
| Chimeric heavy chain 304 | SEQ ID NO: 59 |

TABLE 3

| Antibody 305 | |
|---|---|
| Rabbit variable domain of light chain (VL) | SEQ ID NO: 17 |
| CDR1L | SEQ ID NO: 18 |
| CDR2L | SEQ ID NO: 19 |
| CDR3L | SEQ ID NO: 20 |
| Rabbit variable domain of heavy chain (VH) | SEQ ID NO: 21 |
| CDR1H | SEQ ID NO: 22 |
| CDR2H | SEQ ID NO: 23 |
| CDR3H | SEQ ID NO: 24 |
| Chimeric light chain 305 | SEQ ID NO: 25 |
| Humanized variant of VL, 305-LC1 | SEQ ID NO: 26 |
| Humanized variant of VL, 305-LC2 | SEQ ID NO: 27 |
| Humanized variant of VL, 305-LC3 | SEQ ID NO: 28 |
| Humanized variant of VL, 305-LC4 | SEQ ID NO: 29 |
| Humanized variant of VL, 305-LC5 | SEQ ID NO: 30 |
| Humanized variant of VL, 305-LC6 | SEQ ID NO: 31 |
| Humanized variant of VL, 305-LC7 | SEQ ID NO: 32 |
| Humanized variant of VL, 305-LC8 | SEQ ID NO: 33 |
| Humanized variant of VL, 305-LC9 | SEQ ID NO: 34 |
| Humanized variant of VL, 305-LC10 | SEQ ID NO: 35 |
| Humanized variant of VL, 305-LC11 | SEQ ID NO: 36 |
| Chimeric heavy chain 305 | SEQ ID NO: 37 |
| Humanized variant of VH, 305-HC1 | SEQ ID NO: 38 |
| Humanized variant of VH, 305-HC2 | SEQ ID NO: 39 |
| Humanized variant of VH, 305-HC3 | SEQ ID NO: 40 |
| Humanized variant of VH, 305-HC4 | SEQ ID NO: 41 |
| Humanized variant of VH, 305-HC5 | SEQ ID NO: 42 |
| Humanized variant of VH, 305-HC6 | SEQ ID NO: 43 |
| Humanized variant of VH, 305-HC7 | SEQ ID NO: 44 |

TABLE 3-continued

| Antibody 305 | |
|---|---|
| Humanized variant of VH, 305-HC8 | SEQ ID NO: 45 |
| Humanized variant of VH, 305-HC9 | SEQ ID NO: 46 |
| Humanized variant of VH, 305-HC10 | SEQ ID NO: 47 |
| Humanized variant of VH, 305-HC11 | SEQ ID NO: 48 |

TABLE 4a

| Human constant regions | |
|---|---|
| Human kappa light chain | SEQ ID NO: 49 |
| Human lambda light chain | SEQ ID NO: 50 |
| Human IgG1 (Caucasian Allotype) | SEQ ID NO: 51 |
| Human IgG1 (Afroamerican Allotype) | SEQ ID NO: 52 |
| Human IgG1 LALA-Mutant (Caucasian Allotype) | SEQ ID NO: 53 |
| Human IgG4 | SEQ ID NO: 54 |
| Human IgG4 SPLE-Mutant | SEQ ID NO: 55 |

TABLE 4b

| Human and Murine TWEAK | |
|---|---|
| Human TWEAK | SEQ ID NO: 60 |
| Murine TWEAK | SEQ ID NO: 61 |

The following examples and sequence listing are provided to aid the understanding of the present invention. It is understood that modifications can be made in the procedures set forth without departing from the spirit of the invention.

EXAMPLE 1

Description of Immunization: Immunization of Rabbits with Human/Murine TWEAK

New Zealand White rabbits (*Oryctolagus cuniculus*) were immunized with 400 μg of recombinant human TWEAK at day 0 with complete Freund's adjuvant, with 200 μg of human TWEAK at days 21, 43 and 65 with incomplete Freund's adjuvant and with 200 μg of murine TWEAK at day 85 with incomplete Freund's adjuvant. All immunizations were done subcutaneously at several sites. Sera were prepared at days 77 and 98 for titer determination. The final boost was done by intravenous injection of 200 μg of human and 200 μg of murine soluble TWEAK and antibodies were selected based on their ability to bind human and mouse TWEAK (Example 2), neutralize human and mouse TWEAK-Fn14 interaction (Examples 4 and 5), and inhibit IL8 secretion (Example 6). In addition, the half-life of the antibody-TWEAK complex was investigated (Example 3). Anti-tumor efficacy of the antibody was tested in B16BL6 (murine melanoma; metastatic lung subline of B16), SJSA (osteosarcoma, ATCC CRL-2098) and HCT-116 (colon, ATCC CCL-247) xenograft models.

EXAMPLE 2

Binding to Human and Mouse TWEAK (ELISA)

Binding of anti-TWEAK antibodies to human and mouse TWEAK was determined by ELISA. Human or mouse recombinant TWEAK were immobilized on a 384-well Nunc Maxisorp plate at 1 μg/ml, 25 μl/well, in 0.5 M carbonate coating buffer, pH 9.5, by incubation overnight at 2-8° C. Blocking of the plate with PBS/1% BSA for 1 hour at room temperature was followed by two wash steps (0.1% Tween® 20 in PBS) and incubation with anti-TWEAK antibodies at different concentrations in blocking buffer or hybridoma supernatants of said antibodies for 1 hour at room temperature. After further four washes, antibodies were detected with anti-rabbit-HRP antibody diluted 1:5000 in blocking buffer, for 1 hour at room temperature. Signal was developed by addition of ABTS® (Roche Diagnostics GmbH) for 10-30 minutes after another four wash steps. Absorbance was read out at 405 nm.

EXAMPLE 3

Half-Life Determination of the Antibody-TWEAK Complexes Using Biacore

A Biacore 2000 instrument was used with a Biacore streptavidin coated sensor mounted into the system. The system buffer HBS-ET (10 mM HEPES pH 7.4, 150 mM NaCl, 1 mM EDTA, 0.05% Tween® 20) was used at a flow rate of 100 μl/min. The sample buffer was the system buffer. Biotinylated human soluble TWEAK (amino acids 99-249 of SEQ ID NO: 60) and biotinylated murine soluble TWEAK (amino acids 81-225 of SEQ ID NO: 61) was immobilized on different flow cells on the SA sensor at 150 RU each. The flow cell FC1 was used as a blank reference cell. Each antibody was injected into the system as an analyte at 100 nM at 100 μl/min for 2 min association time. The dissociation of the immune complexes were monitored for 5 min. The sensor surface was washed with HBS-ET for 10 seconds and regenerated using 2×2 minutes injections with 10 mM glycine pH 2.25. This procedure was done at 25° C. The kinetically rate limiting step of the complex dissociation phase in the interval [240 s-300 s] was taken to calculate the dissociation rate kd [1/s] (Biacore Evaluation Software 4.0). According to the equation t1/2 diss=ln(2)/(60×kd), the half-life of the immunocomplexes in minutes was calculated. Results are shown in tables 5a and 5b, as well as in table 6b.

TABLE 5a

| Antibody | | Human TWEAK t/2 diss [min] 25° C. | Murine TWEAK t/2 diss [min] 25° C. |
|---|---|---|---|
| TW-301chi | Chimer[1] | 110 | n.d. |
| TW-304chi | Chimer[1] | 37 | n.d. |
| TW-305chi | Chimer[1] | 147 | 39 |
| Chimeric P2D10 | Chimer[1] | 76 | 41 |

[1] human constant regions of the human kappa light chain constant region of SEQ ID NO: 49 and the human IgG1 constant region of SEQ ID NO: 51

In a further experiment the half-Life of the antibody-TWEAK complexes (t/2 diss [min] at 25° C.) of the chimeric TW-305chi and the chimeric version of P2D10 of WO 2006/130374 was determined (both chimeric antibodies have as human constant regions the human kappa light chain constant region of SEQ ID NO:49 and the human IgG1 constant region of SEQ ID NO: 51)

TABLE 5b

| Antibody | | Human TWEAK t/2 diss [min] 25° C. | Murine TWEAK t/2 diss [min] 25° C. |
|---|---|---|---|
| TW-305chi | Chimer[1] | 148 | 41 |
| Chimeric P2D10 | Chimer[1] | 76 | 41 |

[1] human constant regions of the human kappa light chain constant region of SEQ ID NO: 49 and the human IgG1 constant region of SEQ ID NO: 51

The antibodies according to the invention show valuable properties like a half-life of a complex between soluble human TWEAK (amino acids 99-249 of SEQ ID NO: 60) and antibody of 100 minutes or more, preferably of 110 minutes or more at 25° C., measured by Biacore. Anti-TWEAK antibodies showing such half-life are especially preferred for use in the treatment of autoimmune diseases, rheumatoid arthritis, psoratic arthritis, muscle diseases, e.g. muscular dystrophy, multiple sclerosis, chronic kidney diseases, bone diseases, e.g. bone degeneration in multiple myeloma, systemic lupus erythematosus, lupus nephritis, and vascular injury.

EXAMPLE 4

Neutralization of TWEAK-Fn14 Interaction (Human)

Blocking of human TWEAK/human Fn14 interaction was shown by receptor interaction ELISA. 96-well Maxisorp® plates (Nunc) were coated with 100 µl 1 µg/ml human Fn14:Fc (extracellular domain of human Fn14 (amino acids 1-75) fused to Fc portion of human IgG1) in PBS per well for 1.5 h at room temperature and blocked with a solution of 5% FBS in PBS for 30 minutes at room temperature under shaking. In the meantime, human Flag-tagged soluble TWEAK (amino acids 106-249) at 2.5 ng/ml in blocking solution was incubated with different concentrations of anti-TWEAK antibodies or hybridoma supernatant for 2 hours at room temperature under shaking After washing the Fn14-coated plate once with wash buffer (0.1% Tween® 20 in PBS), 100 µl of the TWEAK-antibody solution were transferred to each well and the plate was incubated for 1 hour at room temperature, followed by four washes with wash buffer. Wells were filled with 100 µl of anti-FLAG-HRP detection antibody, diluted 1:5000 in blocking buffer, and incubated for 1 h at room temperature. After four more wash steps, the signal was developed by addition of 100 µl 3,3,5,5-Tetramethylbenzidine (TMB) solution for approximately ten minutes. The reaction was stopped by adding 100 µl of 1 N HCl, and absorbance measured at 450 nm (reference wavelength 620 nm). Results are shown in table 6.

EXAMPLE 5

Neutralization of TWEAK-Fn14 Interaction (Mouse)

The mouse TWEAK/mouse Fn14 interaction ELISA followed a similar principle as described for the human proteins but used a different detection system, as mouse soluble TWEAK was not tagged. Briefly, Maxisorp plates were coated with mouse Fn14:Fc (extracellular domain of mouse Fn14 (amino acids 1-75) fused to Fc portion of human IgG1) as described above for human Fn14:Fc, followed by blocking and washing. Mouse soluble TWEAK at 4 ng/ml was pre-incubated with anti-TWEAK-antibodies or hybridoma supernatant in blocking buffer and 100 µl of the mixture were added per well of the Fn14-coated plate. After 1 hour of incubation at room temperature and four washes, biotinylated anti-mouse TWEAK antibody at 125 ng/ml in blocking buffer was added for 1 hour at room temperature, followed by another four wash steps. The TWEAK antibody was detected by incubation with streptavidin-HRP, diluted 1:5000 in blocking buffer, for 30 minutes at room temperature. Signal was developed and absorbance measured as described above. Results are shown in table 6a and 6b.

EXAMPLE 6

IL-8 Secretion ELISA

Blocking of TWEAK activity by anti-TWEAK antibodies in a cellular system was shown in an IL-8 secretion assay using A375 melanoma cells. 10,000 A375 cells (ATCC #CRL1619) were seeded per well of 96-well cell culture plate in 100 µl of growth medium (DMEM with 4.5 g/L glucose, with pyruvate and GlutaMAX™/10% FBS) and incubated at 37° C./5% $CO_2$ for 48 hour. Human recombinant soluble TWEAK was pre-incubated at 300 ng/ml with different concentrations of anti-TWEAK antibodies in growth medium for 30 minutes at room temperature. Then, 50 µl of the mixture were added to each well of the cell plate, followed by another 48 hour-incubation to allow for IL-8 secretion. 20 µl of the cell supernatant were removed after centrifuging the plate for five minutes at 200×g and mixed with 980 µl of RD5P Calibrator Diluent from the "CXCL8 Quantikine ELISA" kit (R&D Systems). IL-8 was detected by the ELISA according to the manufacturer's instructions. Results are shown in table 6a and 6b.

TABLE 6a

| | | Inhibition of TWEAK-Fn14 Interaction | | |
|---|---|---|---|---|
| Antibody | | Human TWEAK IC50 [ng/ml] | Murine TWEAK IC50 [ng/ml] | IL-8 Secretion IC50 [ng/ml] |
| TW-301 | Rabbit | 3.4 | 4.7 | 128 |
| TW-304 | Rabbit | 2.8 | 3.6 | 109 |
| TW-305 | Rabbit | 2.5 | 3.3 | 99 |
| TW-301chi | Chimer | 2.8 | 6.4 | 121 |
| TW-304chi | Chimer | 2.6 | 4.4 | 122 |
| TW-305chi | Chimer | 2.6 | 4.9 | 104 |

TABLE 6b

| | | Interaction Inhibition | | | Biacore | | | |
|---|---|---|---|---|---|---|---|---|
| | | Human | Murine | IL8- | t/2 diss. [min] | | | |
| Antibody | SEQ ID NOs | IC50 [ng/ml] | IC50 [ng/ml] | Secretion [ng/ml] | 25° C. human | 25° C. murine | 37° C. human | 37° C. murine |
| 27 | 27, 41 | 2.3 | 8.2 | 197 | 110 | 19 | 147 | 19 |
| 28 | 27, 44 | 1.5 | 6.5 | 165 | 87 | 19 | 115 | 17 |
| 29 | 27, 45 | 1.8 | 5.7 | 78 | 146 | 22 | 195 | 21 |
| 30 | 26, 47 | 2.3 | 7.6 | 207 | 50 | 17 | 45 | 15 |
| 31 | 29, 44 | 1.7 | 7.1 | 94 | 115 | 19 | 151 | 19 |
| 32 | 31, 45 | 1.5 | 5.4 | 134 | 67 | 17 | 50 | 20 |
| 33 | 29, 41 | 1.7 | 6.7 | 26 | 127 | 19 | 99 | 15 |
| 34 | 29, 39 | 1.9 | 5.9 | 24 | 158 | 22 | 185 | 20 |

EXAMPLE 7

Determination of the Epitope Region of TW-301, TW-304, TW-305

A Biacore 2000 instrument was used together with the Biacore Evaluation Software 4.0. The sample and system buffer was HBS-ET pH 7.4. Due to strong unspecific binding of the TWEAK analyte to the sensor surface epitope mapping of individual antibodies could not be done as usual by a Biacore cross-competition experiment as described by Johne, B. et al., J. Immun. Meth. 160 (1993) 191-198.

Because of the individual biochemical properties of the TWEAK protein another method had to be developed using TWEAK as ligand. Biotinylated TWEAK was immobilized on the streptavidin-coated chip surface and epitope coverage of consecutively injected antibodies (antibody 1) was measured. The aim was to detect the relative binding levels of a secondary antibody (antibody 2) in the presence of an already bound primary antibody. From these relative binding levels a quotient was calculated (Ab2/Ab1, molar ratio given in %, table 7).

5 nM of biotinylated TWEAK was immobilized at 20 μl/min for 1 min on a streptavidin coated sensor flow cell. Primary and secondary mAbs were consecutively injected at 10 μl/min for 4 min into the system at 100 nM each until saturation of the respective TWEAK epitopes was achieved. As a reference an SA coated flow cell was used.

The system was washed with HBS-ET for 20 sec at 30 μl/min followed by two regeneration steps with 1 min at 30 μl/min 6 M GuadHCl and 100 mM HCl. These regeneration steps stripped off the bound mAbs from the sensor surface and immobilized biotinylated TWEAK was irreversibly denatured. The process was repeated by the immobilization of native biotinylated TWEAK protein (feed batch mode) on the same flow cell until the streptavidin sensor surface was completely saturated by biotinylated TWEAK.

TABLE 7

| MR % | Antibody 2 | | |
|---|---|---|---|
| Antibody 1 | TW-301chi | TW-304chi | TW-305chi |
| TW-301chi | 0 | 6 | 9 |
| TW-304chi | 0 | 0 | 3 |
| TW-305chi | 0 | 1 | 0 |

The crossblocking experiment shows accessibility values of the respective antibodies smaller than 10%, which is within the noise of this assay. It is clearly shown, that TW-301chi, TW-304chi and TW-305chi bind to the same epitope region.

EXAMPLE 8

In Vivo-Inhibition of Collagen-Induced Arthritis (Murine Model of Rheumatoid Arthritis)—Antibody 305 (Chimeric; TW305) Inhibits Collagen-induced Arthritis in a Murine Model of Rheumatoid Arthritis.

Male DBA1/J mice (Jackson Laboratory, Bar Harbor, Me.), 6 to 8 weeks old, were immunized with type II bovine collagen in complete Freund's adjuvant and again in incomplete Freund's adjuvant 3 weeks later (boost, day 0). Mice were administered with chimeric antibody 305 (=TW305, see FIG. 1) (10 mg/kg, n=12), Enbrel® (10 mg/kg, n=12) or vehicle (phosphate buffered saline, n=12) every other day starting the day before the boost. Mice were examined for arthritis on day 0, 2, 5, 7, 9, 12 and 14 after the boost. Severity of arthritis was scored based on the following criteria: 1=swelling and/or redness of one digit; 2=swelling in two or more joints; 3=gross swelling of the paw with more than two joints involved; 4=severe arthritis of the entire paw and digits. Compared with vehicle, TW-305 significantly reduced clinical scores (p<0.05, day 14), by a similar magnitude to that of the TNF blocker Enbrel®. Results are shown in FIG. 1.

What is claimed is:

1. A chimeric, humanized or T-cell epitope depleted variant antibody binding to human TWEAK, comprising
   a) a variable light chain of SEQ ID NO:1 and a variable heavy chain of SEQ ID NO:5,
   b) a variable light chain of SEQ ID NO:9 and a variable heavy chain of SEQ ID NO:13 or
   c) a variable light chain of SEQ ID NO:17 and a variable heavy chain of SEQ ID NO:21.

2. An antibody binding to human TWEAK, comprising
   a) CDR1H of SEQ ID NO:6, CDR2H of SEQ ID NO:7, CDR3H of SEQ ID NO:8 and CDR1L of SEQ ID NO:2, CDR2L of SEQ ID NO:3, CDR3L of SEQ ID NO:4,
   b) CDR1H of SEQ ID NO:14, CDR2H of SEQ ID NO:15, CDR3H of SEQ ID NO:16 and CDR1L of SEQ ID NO:10, CDR2L of SEQ ID NO:11, CDR3L of SEQ ID NO:12, or
   c) CDR1H of SEQ ID NO:22, CDR2H of SEQ ID NO:23, CDR3H of SEQ ID NO:24 and CDR1L of SEQ ID NO:18, CDR2L of SEQ ID NO:19, CDR3L of SEQ ID NO:20.

3. The antibody of claim 2, comprising CDR1H of SEQ ID NO:6, CDR2H of SEQ ID NO:7, CDR3H of SEQ ID NO:8 and CDR1L of SEQ ID NO:2, CDR2L of SEQ ID NO:3, CDR3L of SEQ ID NO:4.

4. The antibody of claim 2, comprising CDR1H of SEQ ID NO:14, CDR2H of SEQ ID NO:15, CDR3H of SEQ ID NO:16 and CDR1L of SEQ ID NO:10, CDR2L of SEQ ID NO:11, CDR3L of SEQ ID NO:12.

5. The antibody of claim 2, comprising CDR1H of SEQ ID NO:22, CDR2H of SEQ ID NO:23, CDR3H of SEQ ID NO:24 and CDR1L of SEQ ID NO:18, CDR2L of SEQ ID NO:19, CDR3L of SEQ ID NO:20.

6. The antibody of claim 5, comprising:
   a) a variable light chain of SEQ ID NO: 27 and a variable heavy chain of SEQ ID NO: 41,
   b) a variable light chain of SEQ ID NO: 27 and a variable heavy chain of SEQ ID NO: 44,
   c) a variable light chain of SEQ ID NO: 27 and a variable heavy chain of SEQ ID NO: 45,
   d) a variable light chain of SEQ ID NO: 26 and a variable heavy chain of SEQ ID NO: 47,
   e) a variable light chain of SEQ ID NO: 29 and a variable heavy chain of SEQ ID NO: 44,
   f) a variable light chain of SEQ ID NO: 31 and a variable heavy chain of SEQ ID NO: 45,
   g) a variable light chain of SEQ ID NO: 29 and a variable heavy chain of SEQ ID NO: 41,
   or h) a variable light chain of SEQ ID NO: 29 and a variable heavy chain of SEQ ID NO: 39.

7. The antibody of claim 5, comprising a combination of a variable light chain sequence/variable heavy chain sequence selected from the group consisting of SEQ ID NO:1/SEQ ID NO:5, SEQ ID NO:9/SEQ ID NO:13, SEQ ID NO:17/SEQ ID NO:21, SEQ ID NO:25/SEQ ID NO:37, SEQ ID NO:26/SEQ ID NO:38, SEQ ID NO:27/SEQ ID NO:39, SEQ ID NO:28/SEQ ID NO:40, SEQ ID NO:29/SEQ ID NO:41, SEQ ID NO:30/SEQ ID NO:42, SEQ ID NO:31/SEQ ID NO:43, SEQ ID NO:32/SEQ ID NO:44; SEQ ID NO:33/SEQ ID NO:45, SEQ ID NO:34/SEQ ID NO:46, SEQ ID NO:35/SEQ ID NO:47, SEQ ID NO:36/SEQ ID NO:48, SEQ ID NO:56/SEQ ID NO:57, or SEQ ID NO:58/SEQ ID NO:59.

8. The antibody of claim 5, comprising a variable heavy chain or variable light chain selected from the group of variable heavy or light chains of SEQ ID NOs:17, 25, 26, 27, 28, 29, 30, 31, 32, 33, 34, 35, 36, 56, 58, 21, 37, 38, 39, 40, 41, 42, 43, 44, 45, 46, 47, 48, 57, or 59.

9. A composition comprising said anti-TWEAK antibody of claim 2, 5, or 6.

10. The composition of claim 9 further comprising a pharmaceutical carrier.

11. An antibody binding to human TWEAK, comprising
    a) CDR1H of SEQ ID NO:22, CDR2H of SEQ ID NO:23, CDR3H of SEQ ID NO:24 and CDR1L of SEQ ID NO:18, CDR 2L of SEQ ID NO:19, CDR3L of SEQ ID NO:20;
    b) a variable light chain of SEQ ID NO: 27; and
    c) a variable heavy chain of SEQ ID NO: 41.

* * * * *

SEQUENCE LISTING

```
<160> NUMBER OF SEQ ID NOS: 61

<210> SEQ ID NO 1
<211> LENGTH: 111
<212> TYPE: PRT
<213> ORGANISM: Oryctolagus cuniculus

<400> SEQUENCE: 1

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser Ser
                20                  25                  30

Leu Ala Trp Tyr Gln Gln Lys Pro Gly Gln Pro Pro Lys Leu Leu Ile
            35                  40                  45

Tyr Asp Ala Phe Asp Leu Ala Ser Gly Val Ser Ser Arg Phe Thr Gly
        50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Thr Asp Tyr Gly Asn Ser
                85                  90                  95

Trp Asp Gly Asn Pro Phe Gly Gly Gly Thr Glu Val Val Val Thr
            100                 105                 110

<210> SEQ ID NO 2
```

-continued

```
<211> LENGTH: 11
<212> TYPE: PRT
<213> ORGANISM: Oryctolagus cuniculus

<400> SEQUENCE: 2

Gln Ala Ser Gln Ser Ile Tyr Ser Ser Leu Ala
1               5                   10

<210> SEQ ID NO 3
<211> LENGTH: 7
<212> TYPE: PRT
<213> ORGANISM: Oryctolagus cuniculus

<400> SEQUENCE: 3

Asp Ala Phe Asp Leu Ala Ser
1               5

<210> SEQ ID NO 4
<211> LENGTH: 13
<212> TYPE: PRT
<213> ORGANISM: Oryctolagus cuniculus

<400> SEQUENCE: 4

Gln Ser Thr Asp Tyr Gly Asn Ser Trp Asp Gly Asn Pro
1               5                   10

<210> SEQ ID NO 5
<211> LENGTH: 116
<212> TYPE: PRT
<213> ORGANISM: Oryctolagus cuniculus

<400> SEQUENCE: 5

Gln Ser Leu Glu Glu Ser Gly Gly Leu Val Lys Pro Gly Ala Ser
1               5                   10                  15

Leu Thr Leu Thr Cys Thr Ala Ser Gly Phe Thr Phe Asn Ala Asn Tyr
                20                  25                  30

Trp Ile Cys Trp Val Arg Gln Ala Pro Gly Lys Gly Leu Glu Trp Ile
            35                  40                  45

Ala Cys Ile Tyr Gly Gly Gly Asn Ser Gly Ala Tyr Tyr Ala Ser Trp
50                  55                  60

Ala Thr Gly Arg Phe Thr Ile Ser Arg Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Pro Ile Ser Arg Asp Leu Trp Gly Pro Gly Thr Leu Val
                100                 105                 110

Thr Val Ser Leu
        115

<210> SEQ ID NO 6
<211> LENGTH: 7
<212> TYPE: PRT
<213> ORGANISM: Oryctolagus cuniculus

<400> SEQUENCE: 6

Phe Thr Phe Asn Ala Asn Tyr
1               5

<210> SEQ ID NO 7
<211> LENGTH: 6
<212> TYPE: PRT
<213> ORGANISM: Oryctolagus cuniculus
```

```
<400> SEQUENCE: 7

Tyr Gly Gly Gly Asn Ser
1               5

<210> SEQ ID NO 8
<211> LENGTH: 7
<212> TYPE: PRT
<213> ORGANISM: Oryctolagus cuniculus

<400> SEQUENCE: 8

Gly Pro Ile Ser Arg Asp Leu
1               5

<210> SEQ ID NO 9
<211> LENGTH: 111
<212> TYPE: PRT
<213> ORGANISM: Oryctolagus cuniculus

<400> SEQUENCE: 9

Asp Val Val Met Thr Gln Thr Pro Ser Pro Val Ser Ala Ala Val Gly
1               5                   10                  15

Gly Thr Val Thr Ile Lys Cys Gln Ala Ser Gln Ser Ile Gly Asn Asp
            20                  25                  30

Leu Ser Trp Tyr Gln Gln Lys Pro Gly Gln Arg Pro Lys Leu Leu Ile
        35                  40                  45

Tyr Ser Val Ser Thr Leu Ala Ser Gly Val Pro Ser Arg Phe Lys Gly
    50                  55                  60

Ser Gly Ser Gly Thr Glu Tyr Ser Leu Thr Ile Ser Asp Val Gln Cys
65                  70                  75                  80

Ala Asp Ala Ala Thr Tyr Tyr Cys Gln Cys Ile Asp Tyr Gly Asn Asn
                85                  90                  95

Tyr Val Gly Asn Thr Phe Gly Gly Gly Thr Glu Val Val Val Lys
            100                 105                 110

<210> SEQ ID NO 10
<211> LENGTH: 11
<212> TYPE: PRT
<213> ORGANISM: Oryctolagus cuniculus

<400> SEQUENCE: 10

Gln Ala Ser Gln Ser Ile Gly Asn Asp Leu Ser
1               5                   10

<210> SEQ ID NO 11
<211> LENGTH: 7
<212> TYPE: PRT
<213> ORGANISM: Oryctolagus cuniculus

<400> SEQUENCE: 11

Ser Val Ser Thr Leu Ala Ser
1               5

<210> SEQ ID NO 12
<211> LENGTH: 13
<212> TYPE: PRT
<213> ORGANISM: Oryctolagus cuniculus

<400> SEQUENCE: 12

Gln Cys Ile Asp Tyr Gly Asn Asn Tyr Val Gly Asn Thr
1               5                   10
```

<210> SEQ ID NO 13
<211> LENGTH: 116
<212> TYPE: PRT
<213> ORGANISM: Oryctolagus cuniculus

<400> SEQUENCE: 13

Gln Ser Leu Glu Glu Ser Gly Gly Asp Leu Val Lys Pro Gly Ala Ser
1               5                   10                  15

Leu Thr Leu Thr Cys Lys Ala Ser Gly Phe Ser Phe Ser Ser Thr Tyr
            20                  25                  30

Tyr Met Cys Trp Val Arg Gln Ala Pro Gly Lys Gly Leu Glu Trp Ile
        35                  40                  45

Gly Cys Ile Tyr Val Gly Ser Ser Gly Ala Pro Tyr Tyr Ala Ser Trp
    50                  55                  60

Ala Lys Gly Arg Phe Thr Ile Ser Lys Thr Ser Ser Thr Thr Val Ala
65                  70                  75                  80

Leu Gln Met Thr Ser Leu Thr Pro Ala Asp Thr Ala Thr Tyr Val Cys
                85                  90                  95

Thr Arg Ser Val His Phe Gly Asp Leu Trp Gly Pro Gly Thr Leu Val
            100                 105                 110

Thr Val Ser Ser
            115

<210> SEQ ID NO 14
<211> LENGTH: 7
<212> TYPE: PRT
<213> ORGANISM: Oryctolagus cuniculus

<400> SEQUENCE: 14

Phe Ser Phe Ser Ser Thr Tyr
1               5

<210> SEQ ID NO 15
<211> LENGTH: 6
<212> TYPE: PRT
<213> ORGANISM: Oryctolagus cuniculus

<400> SEQUENCE: 15

Tyr Val Gly Ser Ser Gly
1               5

<210> SEQ ID NO 16
<211> LENGTH: 7
<212> TYPE: PRT
<213> ORGANISM: Oryctolagus cuniculus

<400> SEQUENCE: 16

Ser Val His Phe Gly Asp Leu
1               5

<210> SEQ ID NO 17
<211> LENGTH: 111
<212> TYPE: PRT
<213> ORGANISM: Oryctolagus cuniculus

<400> SEQUENCE: 17

Ala Ile Glu Met Thr Gln Thr Pro Phe Ser Val Ser Ala Ala Val Gly
1               5                   10                  15

Gly Thr Val Thr Ile Asn Cys Gln Ala Ser Gln Asn Ile Tyr Ser Asn
            20                  25                  30

```
Leu Ala Trp Tyr Gln Gln Lys Pro Gly Gln Pro Pro Lys Leu Leu Met
             35                  40                  45

Tyr Thr Ala Ser Tyr Leu Ala Ser Gly Val Pro Ser Arg Phe Lys Gly
     50                  55                  60

Ser Gly Ser Arg Thr Glu Tyr Thr Leu Thr Ile Ser Gly Val Gln Cys
 65                  70                  75                  80

Ala Asp Ala Ala Thr Tyr Tyr Cys Gln Thr Ala Tyr Tyr Asn Ser Arg
                 85                  90                  95

Pro Asp Thr Val Ala Phe Gly Gly Gly Thr Glu Val Val Val Lys
                100                 105                 110
```

<210> SEQ ID NO 18
<211> LENGTH: 11
<212> TYPE: PRT
<213> ORGANISM: Oryctolagus cuniculus

<400> SEQUENCE: 18

```
Gln Ala Ser Gln Asn Ile Tyr Ser Asn Leu Ala
 1               5                  10
```

<210> SEQ ID NO 19
<211> LENGTH: 7
<212> TYPE: PRT
<213> ORGANISM: Oryctolagus cuniculus

<400> SEQUENCE: 19

```
Thr Ala Ser Tyr Leu Ala Ser
 1               5
```

<210> SEQ ID NO 20
<211> LENGTH: 13
<212> TYPE: PRT
<213> ORGANISM: Oryctolagus cuniculus

<400> SEQUENCE: 20

```
Gln Thr Ala Tyr Tyr Asn Ser Arg Pro Asp Thr Val Ala
 1               5                  10
```

<210> SEQ ID NO 21
<211> LENGTH: 120
<212> TYPE: PRT
<213> ORGANISM: Oryctolagus cuniculus

<400> SEQUENCE: 21

```
Gln Glu Gln Leu Val Glu Ser Gly Gly Gly Leu Val Gln Pro Gly Gly
 1               5                  10                  15

Ser Leu Thr Leu Ser Cys Lys Ala Ser Gly Phe Asp Phe Ser Thr Tyr
             20                  25                  30

Tyr Met Ser Trp Val Arg Gln Ala Pro Gly Lys Gly Leu Glu Trp Ile
             35                  40                  45

Gly Thr Val Tyr Val Arg Gln Gly Thr Thr Tyr Tyr Ala Ser Trp Leu
     50                  55                  60

Asn Gly Arg Phe Thr Ile Ser Ser Asp Asn Ala Gln Asn Thr Val Asp
 65                  70                  75                  80

Leu Lys Met Asn Ser Leu Thr Ala Ala Asp Thr Ala Thr Tyr Phe Cys
                 85                  90                  95

Ala Lys Gly Gly Tyr Asn Tyr Asp Asp Ala Phe Val Ile Trp Gly Pro
                100                 105                 110

Gly Thr Leu Val Thr Val Ser Phe
                115                 120
```

<210> SEQ ID NO 22
<211> LENGTH: 7
<212> TYPE: PRT
<213> ORGANISM: Oryctolagus cuniculus

<400> SEQUENCE: 22

Gly Phe Asp Phe Ser Thr Tyr
1               5

<210> SEQ ID NO 23
<211> LENGTH: 6
<212> TYPE: PRT
<213> ORGANISM: Oryctolagus cuniculus

<400> SEQUENCE: 23

Tyr Val Arg Gln Gly Thr
1               5

<210> SEQ ID NO 24
<211> LENGTH: 11
<212> TYPE: PRT
<213> ORGANISM: Oryctolagus cuniculus

<400> SEQUENCE: 24

Gly Gly Tyr Asn Tyr Asp Asp Ala Phe Val Ile
1               5                   10

<210> SEQ ID NO 25
<211> LENGTH: 218
<212> TYPE: PRT
<213> ORGANISM: Artificial
<220> FEATURE:
<223> OTHER INFORMATION: Antibody 305, Chimeric light chain

<400> SEQUENCE: 25

Ala Ile Glu Met Thr Gln Thr Pro Phe Ser Val Ser Ala Ala Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Pro Pro Lys Leu Leu Met
        35                  40                  45

Tyr Thr Ala Ser Tyr Leu Ala Ser Gly Val Pro Ser Arg Phe Lys Gly
    50                  55                  60

Ser Gly Ser Arg Thr Glu Tyr Thr Leu Thr Ile Ser Gly Val Gln Cys
65                  70                  75                  80

Ala Asp Ala Ala Thr Tyr Tyr Cys Gln Thr Ala Tyr Tyr Asn Ser Arg
                85                  90                  95

Pro Asp Thr Val Ala Phe Gly Gly Thr Glu Val Val Val Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

```
His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 26
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC1

<400> SEQUENCE: 26

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 27
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC2

<400> SEQUENCE: 27

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 28
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC3
```

```
<400> SEQUENCE: 28

Ala Ile Arg Met Thr Gln Ser Pro Ser Ser Phe Ser Ala Ser Thr Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 29
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC4

<400> SEQUENCE: 29

Ala Ile Arg Met Thr Gln Ser Pro Ser Ser Phe Ser Ala Ser Thr Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Cys Leu Gln Ser
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 30
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC5

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60
```

```
Ser Gly Ser Gly Thr Glu Tyr Thr Leu Thr Ile Ser Ser Leu Gln Pro
 65                  70                  75                  80

Asp Asp Phe Ala Thr Tyr Tyr Cys Gln Thr Ala Tyr Tyr Asn Ser Arg
                 85                  90                  95

Pro Asp Thr Val Ala Phe Gly Gly Gly Thr Lys Val Glu Ile Lys
                100                 105                 110

<210> SEQ ID NO 31
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC6

<400> SEQUENCE: 31

Asp Ile Gln Met Thr Gln Ser Pro Ser Thr Leu Ser Ala Ser Val Gly
  1               5                  10                  15

Asp Arg Val Thr Ile Thr Cys Gln Ala Ser Gln Asn Ile Tyr Ser Asn
                 20                  25                  30

Leu Ala Trp Tyr Gln Gln Lys Pro Gly Lys Ala Pro Lys Leu Leu Ile
             35                  40                  45

Tyr Thr Ala Ser Tyr Leu Ala Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Thr Ala Tyr Tyr Asn Ser Arg
                 85                  90                  95

Pro Asp Thr Val Ala Phe Gly Gly Gly Thr Lys Val Glu Ile Lys
                100                 105                 110

<210> SEQ ID NO 32
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC7

<400> SEQUENCE: 32

Asp Ile Gln Met Thr Gln Ser Pro Ser Val Ser Ala Ser Val Gly
  1               5                  10                  15

Gly Thr Val Thr Ile Thr Cys Gln Ala Ser Gln Asn Ile Tyr Ser Asn
                 20                  25                  30

Leu Ala Trp Tyr Gln Gln Lys Pro Gly Lys Ala Pro Lys Leu Leu Ile
             35                  40                  45

Tyr Thr Ala Ser Tyr Leu Ala Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Thr Ala Tyr Tyr Asn Ser Arg
                 85                  90                  95

Pro Asp Thr Val Ala Phe Gly Gly Gly Thr Lys Val Glu Ile Lys
                100                 105                 110

<210> SEQ ID NO 33
<211> LENGTH: 111
<212> TYPE: PRT
<213> ORGANISM: Artificial
<220> FEATURE:
```

<223> OTHER INFORMATION: Antibody 305, Humanized variant of variable
      domain of light chain (VL), 305-LC8

<400> SEQUENCE: 33

Asp Ile Gln Met Thr Gln Ser Pro Ser Ser Val Ser Ala Ser Val Gly
1               5                   10                  15

Asp Arg Val Thr Ile Asn Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 34
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC9

<400> SEQUENCE: 34

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Gln Pro Pro Lys Leu Leu Ile
        35                  40                  45

Tyr Thr Ala Ser Tyr Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Ala Tyr Tyr Asn Ser Arg
                85                  90                  95

Pro Asp Thr Val Ala Phe Gly Gly Gly Thr Lys Val Glu Ile Lys
            100                 105                 110

<210> SEQ ID NO 35
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC10

<400> SEQUENCE: 35

Asp Ile Gln Met Thr Gln Ser Pro Ser Ser Val Ser Ala Ser Val Gly
1               5                   10                  15

Asp Arg Val Thr Ile Thr Cys Gln Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Thr Ala Ser Tyr Leu Ala Ser Gly Val Pro Ser Arg Phe Lys Gly

```
                 50                  55                  60
Ser Gly Ser Arg Thr Asp Tyr Thr Leu Thr Ile Ser Ser Leu Gln Pro
 65                  70                  75                  80

Glu Asp Phe Ala Thr Tyr Tyr Cys Gln Thr Ala Tyr Tyr Asn Ser Arg
                 85                  90                  95

Pro Asp Thr Val Ala Phe Gly Gly Gly Thr Lys Val Glu Ile Lys
                100                 105                 110
```

<210> SEQ ID NO 36
<211> LENGTH: 111
<212> TYPE: PRT
<213> ORGANISM: Artificial
<220> FEATURE:
<223> OTHER INFORMATION: Antibody 305, Humanized variant of variable
      domain of light chain (VL), 305-LC11

<400> SEQUENCE: 36

```
Asp Ile Gln Met Thr Gln Ser Pro Ser Ser Val Ser Ala Ser Val Gly
 1               5                  10                  15

Asp Arg Val Thr Ile Thr Cys Gln Ala Ser Gln Asn Ile Tyr Ser Asn
                 20                  25                  30

Leu Ala Trp Tyr Gln Gln Lys Pro Gly Lys Ala Pro Lys Leu Leu Ile
             35                  40                  45

Tyr Thr Ala Ser Tyr Leu Ala Ser Gly Val Pro Ser Arg Phe Ser Gly
         50                  55                  60

Ser Gly Ser Gly Thr Asp Tyr Thr Leu Thr Ile Ser Ser Leu Gln Pro
 65                  70                  75                  80

Ala Asp Ala Ala Thr Tyr Tyr Cys Gln Thr Ala Tyr Tyr Asn Ser Arg
                 85                  90                  95

Pro Asp Thr Val Ala Phe Gly Gly Gly Thr Lys Val Glu Ile Lys
                100                 105                 110
```

<210> SEQ ID NO 37
<211> LENGTH: 450
<212> TYPE: PRT
<213> ORGANISM: Artificial
<220> FEATURE:
<223> OTHER INFORMATION: Antibody 305, Chimeric heavy chain

<400> SEQUENCE: 37

```
Gln Glu Gln Leu Val Glu Ser Gly Gly Gly Leu Val Gln Pro Gly Gly
 1               5                  10                  15

Ser Leu Thr Leu Ser Cys Lys Ala Ser Gly Phe Asp Phe Ser Thr Tyr
                 20                  25                  30

Tyr Met Ser Trp Val Arg Gln Ala Pro Gly Lys Gly Leu Glu Trp Ile
             35                  40                  45

Gly Thr Val Tyr Val Arg Gln Gly Thr Thr Tyr Tyr Ala Ser Trp Leu
         50                  55                  60

Asn Gly Arg Phe Thr Ile Ser Ser Asp Asn Ala Gln Asn Thr Val Asp
 65                  70                  75                  80

Leu Lys Met Asn Ser Leu Thr Ala Ala Asp Thr Ala Thr Tyr Phe Cys
                 85                  90                  95

Ala Lys Gly Gly Tyr Asn Tyr Asp Ala Phe Val Ile Trp Gly Pro
                100                 105                 110

Gly Thr Leu Val Thr Val Ser Phe Ala Ser Thr Lys Gly Pro Ser Val
             115                 120                 125

Phe Pro Leu Ala Pro Ser Ser Lys Ser Thr Ser Gly Gly Thr Ala Ala
         130                 135                 140
```

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 38
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC1

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val

```
                    35                  40                  45
Ser Thr Val Tyr Val Arg Gln Gly Thr Thr Tyr Tyr Ala Ser Trp Leu
        50                  55                  60

Asn Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 39
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC2

<400> SEQUENCE: 39

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Asp Phe Ser Thr Tyr
                20                  25                  30

Tyr Met Ser Trp Val Arg Gln Ala Pro Gly Lys Gly Leu Glu Trp Val
                35                  40                  45

Ser Thr Val Tyr Val Arg Gln Gly Thr Thr Tyr Tyr Ala Ser Trp Leu
        50                  55                  60

Asn Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 40
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC3

<400> SEQUENCE: 40

Gln Val Gln Leu Val Gln Ser Gly Ser Glu Leu Lys Lys Pro Gly Ala
 1               5                  10                  15

Ser Val Lys Val Ser Cys Lys Ala Ser Gly Phe Asp Phe Ser Thr Tyr
                20                  25                  30

Tyr Met Ser Trp Val Arg Gln Ala Pro Gly Gln Gly Leu Glu Trp Met
                35                  40                  45

Gly Thr Val Tyr Val Arg Gln Gly Thr Thr Tyr Tyr Ala Ser Trp Leu
        50                  55                  60

Asn Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
```

```
                     85                  90                  95

Ala Arg Gly Gly Tyr Asn Tyr Asp Asp Ala Phe Val Ile Trp Gly Gln
                100                 105                 110

Gly Thr Leu Val Thr Val Ser Ser
        115                 120

<210> SEQ ID NO 41
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC4

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asp Phe Ser Thr Tyr
                20                  25                  30

Tyr Met Ser Trp Val Arg Gln Ala Pro Gly Gln Gly Leu Glu Trp Met
            35                  40                  45

Gly Thr Val Tyr Val Arg Gln Gly Thr Thr Tyr Tyr Ala Ser Trp Leu
        50                  55                  60

Asn Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Asn Tyr Asp Asp Ala Phe Val Ile Trp Gly Gln
                100                 105                 110

Gly Thr Leu Val Thr Val Ser Ser
        115                 120

<210> SEQ ID NO 42
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC5

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
                20                  25                  30

Tyr Met Ser Trp Val Arg Gln Ala Pro Gly Lys Gly Leu Glu Trp Val
            35                  40                  45

Ser Thr Val Tyr Val Arg Gln Gly Thr Thr Tyr Tyr Ala Ser Trp Leu
        50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asn Tyr Asp Asp Ala Phe Val Ile Trp Gly Gln
                100                 105                 110

Gly Thr Leu Val Thr Val Ser Ser
        115                 120
```

```
<210> SEQ ID NO 43
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC6

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC7

<400> SEQUENCE: 44

Glu Val Gln Leu Leu Glu Ser Gly Gly Gly Leu Val Gln Pro Gly Gly
1               5                   10                  15

Ser Leu Thr Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 45
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC8

<400> SEQUENCE: 45
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 46
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC9

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
    50                  55                  60

Asn Gly Arg Phe Thr Ile Ser Arg Asp Asn Ser Lys Asn Thr Leu Tyr
65                  70                  75                  80

Leu Lys Met Asn Ser Leu Arg Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
        115                 120

<210> SEQ ID NO 47
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC10

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
            50                  55                  60

Asn Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 48
<211> LENGTH: 120
<212> TYPE: PRT
<213> ORGANISM: Artificial
<220> FEATURE:
<223> OTHER INFORMATION: Antibody 305, Humanized variant of variable
      domain of heavy chain (VH), 305-HC11

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Thr Tyr
            20                  25                  30

Tyr Met Ser Trp Val Arg Gln Ala Pro Gly Lys Gly Leu Glu Trp Val
        35                  40                  45

Ser Thr Val Tyr Val Arg Gln Gly Thr Thr Tyr Tyr Ala Ser Trp Leu
            50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Ala Asp Thr Ala Val Tyr Tyr Cys
                85                  90                  95

Ala Lys Gly Gly Tyr Asn Tyr Asp Asp Ala Phe Val Ile Trp Gly Gln
            100                 105                 110

Gly Thr Leu Val Thr Val Ser Ser
            115                 120

<210> SEQ ID NO 49
<211> LENGTH: 107
<212> TYPE: PRT
<213> ORGANISM: homo sapiens

<400> SEQUENCE: 49

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 50
<211> LENGTH: 105
<212> TYPE: PRT
<213> ORGANISM: homo sapiens

<400> SEQUENCE: 50

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 51
<211> LENGTH: 330
<212> TYPE: PRT
<213> ORGANISM: homo sapiens

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 52
<211> LENGTH: 330
<212> TYPE: PRT
<213> ORGANISM: homo sapiens

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn

```
            260                 265                 270
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 53
<211> LENGTH: 330
<212> TYPE: PRT
<213> ORGANISM: homo sapiens

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 327
<212> TYPE: PRT
<213> ORGANISM: homo sapiens

<400> SEQUENCE: 54

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 55

<211> LENGTH: 327
<212> TYPE: PRT
<213> ORGANISM: homo sapiens

<400> SEQUENCE: 55

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 56
<211> LENGTH: 218
<212> TYPE: PRT
<213> ORGANISM: Artificial
<220> FEATURE:
<223> OTHER INFORMATION: Antibody 301, Chimeric light chain

<400> SEQUENCE: 56

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Tyr Ser Ser
                20                  25                  30

Leu Ala Trp Tyr Gln Gln Lys Pro Gly Gln Pro Pro Lys Leu Leu Ile
            35                  40                  45

Tyr Asp Ala Phe Asp Leu Ala Ser Gly Val Ser Ser Arg Phe Thr Gly
50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Gln Ser Thr Asp Tyr Gly Asn Ser
                85                  90                  95

Trp Asp Gly Asn Pro Phe Gly Gly Thr Glu Val Val Val Thr Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 57
<211> LENGTH: 446
<212> TYPE: PRT
<213> ORGANISM: Artificial
<220> FEATURE:
<223> OTHER INFORMATION: Antibody 301, Chimeric heavy chain

<400> SEQUENCE: 57

Gln Ser Leu Glu Glu Ser Gly Gly Gly Leu Val Lys Pro Gly Ala Ser
1               5                   10                  15

Leu Thr Leu Thr Cys Thr Ala Ser Gly Phe Thr Phe Asn Ala Asn Tyr
                20                  25                  30

Trp Ile Cys Trp Val Arg Gln Ala Pro Gly Lys Gly Leu Glu Trp Ile
            35                  40                  45

Ala Cys Ile Tyr Gly Gly Asn Ser Gly Ala Tyr Tyr Ala Ser Trp
50                  55                  60

Ala Thr Gly Arg Phe Thr Ile Ser Arg Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Pro Ile Ser Arg Asp Leu Trp Gly Pro Gly Thr Leu Val
                100                 105                 110

Thr Val Ser Leu Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 58
<211> LENGTH: 218
<212> TYPE: PRT
<213> ORGANISM: Artificial
<220> FEATURE:
<223> OTHER INFORMATION: Antibody 304, Chimeric light chain

<400> SEQUENCE: 58

Asp Val Val Met Thr Gln Thr Pro Ser Pro Val Ser Ala Ala Val Gly
1               5                   10                  15

Gly Thr Val Thr Ile Lys Cys Gln Ala Ser Gln Ser Ile Gly Asn Asp
            20                  25                  30

Leu Ser Trp Tyr Gln Gln Lys Pro Gly Gln Arg Pro Lys Leu Leu Ile
        35                  40                  45

Tyr Ser Val Ser Thr Leu Ala Ser Gly Val Pro Ser Arg Phe Lys Gly
    50                  55                  60

Ser Gly Ser Gly Thr Glu Tyr Ser Leu Thr Ile Ser Asp Val Gln Cys
 65                  70                  75                  80

Ala Asp Ala Ala Thr Tyr Tyr Cys Gln Cys Ile Asp Tyr Gly Asn Asn
                 85                  90                  95

Tyr Val Gly Asn Thr Phe Gly Gly Thr Glu Val Val Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 59
<211> LENGTH: 446
<212> TYPE: PRT
<213> ORGANISM: Artificial
<220> FEATURE:
<223> OTHER INFORMATION: Antibody 304, Chimeric heavy chain

<400> SEQUENCE: 59

Gln Ser Leu Glu Glu Ser Gly Gly Asp Leu Val Lys Pro Gly Ala Ser
1               5                   10                  15

Leu Thr Leu Thr Cys Lys Ala Ser Gly Phe Ser Phe Ser Ser Thr Tyr
            20                  25                  30

Tyr Met Cys Trp Val Arg Gln Ala Pro Gly Lys Gly Leu Glu Trp Ile
        35                  40                  45

Gly Cys Ile Tyr Val Gly Ser Ser Gly Ala Pro Tyr Tyr Ala Ser Trp
    50                  55                  60

Ala Lys Gly Arg Phe Thr Ile Ser Lys Thr Ser Ser Thr Thr Val Ala
65                  70                  75                  80

Leu Gln Met Thr Ser Leu Thr Pro Ala Asp Thr Ala Thr Tyr Val Cys
                85                  90                  95

Thr Arg Ser Val His Phe Gly Asp Leu Trp Gly Pro Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 60
<211> LENGTH: 249
<212> TYPE: PRT
<213> ORGANISM: Homo sapiens

<400> SEQUENCE: 60

Met Ala Ala Arg Arg Ser Gln Arg Arg Arg Gly Arg Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
        35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Ala Arg Ile Asn Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
                180                 185                 190

Glu Glu Phe Ser Ala Thr Ala Ala Ser Ser Leu Gly Pro Gln Leu Arg
                195                 200                 205

Leu Cys Gln Val Ser Gly Leu Leu Ala Leu Arg Pro Gly Ser Ser Leu
        210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245

<210> SEQ ID NO 61
<211> LENGTH: 249
<212> TYPE: PRT
<213> ORGANISM: Mus musculus

<400> SEQUENCE: 61

Met Ala Ala Arg Arg Ser Gln Arg Arg Arg Gly Arg Arg Gly Glu Pro
1               5                   10                  15

Gly Thr Ala Leu Leu Ala Pro Leu Val Leu Ser Leu Gly Leu Ala Leu
                20                  25                  30

Ala Cys Leu Gly Leu Leu Leu Val Val Ser Leu Gly Ser Trp Ala
            35                  40                  45

Thr Leu Ser Ala Gln Glu Pro Ser Gln Glu Glu Leu Thr Ala Glu Asp
        50                  55                  60

Arg Arg Glu Pro Pro Glu Leu Asn Pro Gln Thr Glu Glu Ser Gln Asp
65                  70                  75                  80

Val Val Pro Phe Leu Glu Gln Leu Val Arg Pro Arg Arg Ser Ala Pro
                85                  90                  95

Lys Gly Arg Lys Ala Arg Pro Arg Arg Ala Ile Ala Ala His Tyr Glu
            100                 105                 110

Val His Pro Arg Pro Gly Gln Asp Gly Ala Gln Ala Gly Val Asp Gly
        115                 120                 125

Thr Val Ser Gly Trp Glu Glu Thr Lys Ile Asn Ser Ser Ser Pro Leu
    130                 135                 140

Arg Tyr Asp Arg Gln Ile Gly Glu Phe Thr Val Ile Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asn Gly Val Leu Ala Leu Arg Cys Leu
                180                 185                 190

Glu Glu Phe Ser Ala Thr Ala Ala Ser Ser Pro Gly Pro Gln Leu Arg
                195                 200                 205

Leu Cys Gln Val Ser Gly Leu Leu Pro Leu Arg Pro Gly Ser Ser Leu
        210                 215                 220

Arg Ile Arg Thr Leu Pro Trp Ala His Leu Lys Ala Ala Pro Phe Leu
225                 230                 235                 240

```
Thr Tyr Phe Gly Leu Phe Gln Val His
                245
```